(12) United States Patent
Zhang et al.

(10) Patent No.: US 6,217,827 B1
(45) Date of Patent: Apr. 17, 2001

(54) HYDRIDE GAS DETECTING TAPE

(75) Inventors: Jingnian Zhang, Schaumburg; Roberta L. McMahon, Winnetka, both of IL (US)

(73) Assignee: Zellweger Analytics, Inc., Lincolnshire, IL (US)

( * ) Notice: Subject to any disclaimer, the term of this patent is extended or adjusted under 35 U.S.C. 154(b) by 0 days.

(21) Appl. No.: 09/276,274

(22) Filed: Mar. 25, 1999

(51) Int. Cl.[7] ................. G01N 21/78; G01J 1/50
(52) U.S. Cl. ................. 422/56; 422/86; 436/80; 436/103; 436/106; 436/169
(58) Field of Search ............ 422/56, 86; 436/80, 436/103, 106, 169

(56) References Cited

U.S. PATENT DOCUMENTS

| | | | |
|---|---|---|---|
| 1,321,062 | * 11/1919 | Lamb et al. | 436/134 |
| 2,864,725 | * 12/1958 | Sorg et al. | 427/384 |
| 3,112,998 | * 12/1963 | Grosskopf | 422/60 |
| 4,420,567 | 12/1983 | McMahon et al. | 436/169 |
| 4,643,979 | 2/1987 | Funahashi et al. | 436/78 |
| 4,696,906 | 9/1987 | Funahashi et al. | 436/78 |
| 5,250,260 | 10/1993 | Nakano et al. | 422/56 |
| 5,397,536 | 3/1995 | Nakano et al. | 422/56 |
| 5,665,313 | * 9/1997 | Shimada et al. | 422/86 |
| 5,827,947 | 10/1998 | Miller et al. | 73/24.06 |

FOREIGN PATENT DOCUMENTS 2132413   3/1995  (CA).
WO 90 13925  11/1990  (WO).

* cited by examiner

*Primary Examiner*—Jill Warden
*Assistant Examiner*—LaToya Cross
(74) *Attorney, Agent, or Firm*—Piper Marbury Rudnick & Wolfe

(57) ABSTRACT

A substrate such as a porous tape coated with an adsorbent and impregnated with a processing solution which includes a silver salt, an organic acid such as benzenetricarboxylic acid or benzenesulfonic acid (with or without the addition of nitric acid) and a glycol is a sensitive detecting means for hydride gases and is stable upon exposure to light.

15 Claims, 4 Drawing Sheets

HYDRIDE GAS DETECTING TAPE

BACKGROUND OF THE INVENTION

1. Field of the Invention

The present invention relates in general to the detection and monitoring of dangerous vapors and gases, and, in particular, to a tape for detecting the presence of hydride gases and for optically determining the concentration of hydride gases.

2. Description of Related Art

The semiconductor industry uses a number of hydride gases, particularly arsine, germane, silane, phosphine, and diborane, in the manufacture of semiconductor devices. These hydride gases are either highly toxic or highly flammable, so that the detection of even small concentrations of these gases is crucial. Moreover, industry guidelines recommend threshold limit values (TLVs) for each of these gases which represent the maximum time-weighted average concentration a worker should be exposed to in an eight hour period. As these gases are colorless, non-irritating, and have only a mild odor, various systems for their detection have been proposed.

One approach has been to provide a detection tape that changes color, i.e., forms a stain, in the presence of hydride gases. The intensity of the stain, which is related to the concentration of hydride gas to which the tape has been exposed, is typically measured optically, such as by using a photocell to measure the intensity of light reflected from the stain. A number of different formulations for such hydride detection tapes have been proposed.

U.S. Pat. No. 4,420,567, which is incorporated herein by reference, discloses a hydride detection tape and a tape reader that continuously monitors the hydride gas concentration by measuring the intensity of the stain formed on the detection tape. The disclosed detection tape comprises a porous tape, made of cellulose, incorporating an adsorbent material therein, such as silicic acid, magnesium silicate, magnesium oxide, or aluminum oxide, and impregnated with a processing solution consisting essentially of: (1) silver nitrate, present in an amount of 0.5% to 2.0% by weight; (2) an acid, preferably nitric acid, present in an amount of 0.1 to 5.0% by volume; (3) a glycol, such as ethylene glycol, propylene glycol, trimethylene glycol, or glycerol, present in an amount of 5 to 20% by volume, and (4) an alcohol, such as methanol, ethanol, or isopropanol.

As was disclosed in that patent, it is known that silver nitrate will react with certain metal hydrides to form a characteristic black or dark brown color. However, a detection tape simply coated with silver nitrate is extremely light sensitive and unstable, turning brown within a 24 hour period, even when sealed in a black, lightproof container. The hydride detection tape formulation disclosed in that patent has the advantage of being both sensitive to hydride gases and resistant to light. It is believed that the acid used in the solution is responsible for rendering the silver nitrate resistant to light.

The tape reader disclosed in that patent operates by moving the detection tape past an optical reader that measures the stain intensity by using a photocell to measure the intensity of the light reflected from the tape. The reader also provides outputs indicative of the measured hydride concentration and of the time-weighted average hydride concentration in a given time period.

It has been found that the nitric acid used in the processing solution of this hydride tape gradually weakens the tape over time, apparently by reacting with the cellulose, thereby limiting the tape's useful life to four to six weeks. The weakening has also been found to be more rapid with elevated temperatures. Eventually the tape may become too weak to work in the tape reader. For example, some tape readers are not able to advance tape if it has a tensile strength below about a 1 kg. for most devices.

Patent application WO 90/13025 claims that using p-toluenesulfonic acid instead of nitric acid can increase the mechanical strength of the detection tape. In particular, this reference discloses a hydride detection tape comprising a support, composed mainly of cellulosic material, coated with an adsorbent and a solution comprising: (1) silver nitrate present in an amount of 0.5 to 2.0% by weight; (2) a polyvalent alcohol humectant, such as ethylene glycol, propylene glycol, trimethylene glycol, glycerine, or mixtures thereof, present in an amount of 5 to 30% by weight; (3) p-toluenesulfonic acid, present in amount of 0.5 to 3.0% by weight; and (4) an organic solvent, such as ethanol, methanol, or acetone.

However, it has been found that when p-toluenesulfonic acid is used in place of nitric acid the resulting hydride detection tape still weakens more quickly than desired. Additionally, the resulting detection tape exhibits a sensitivity to silane and germane that is undesirably low.

SUMMARY OF THE INVENTION

The principle object of the present invention is to provide a hydride detection tape that maintains a high tensile strength over a longer period of time.

Another object of the present invention is to provide a hydride detection tape that maintains a high tensile strength after exposure to elevated temperatures.

Yet another object of the present invention is to provide a hydride detection tape that is also highly sensitive to several of the following gases: arsine, diborane, germane, silane, and phosphine.

A further object of the present invention is to provide a hydride detection tape that is resistant to light.

In accordance with the present invention, a detection tape for detecting hydride gases, such as arsine, germane, silane, diborane, and phoshine, is provided. The detection tape comprises a cellulose-based porous tape incorporating an adsorbent, and impregnated with a solution comprising an alcohol, a glycol, silver nitrate, and an organic acid, wherein the organic acid is preferably 1,2,4-benzenetricarboxylic acid.

DESCRIPTION OF THE PREFERRED EMBODIMENT

Figure 1:
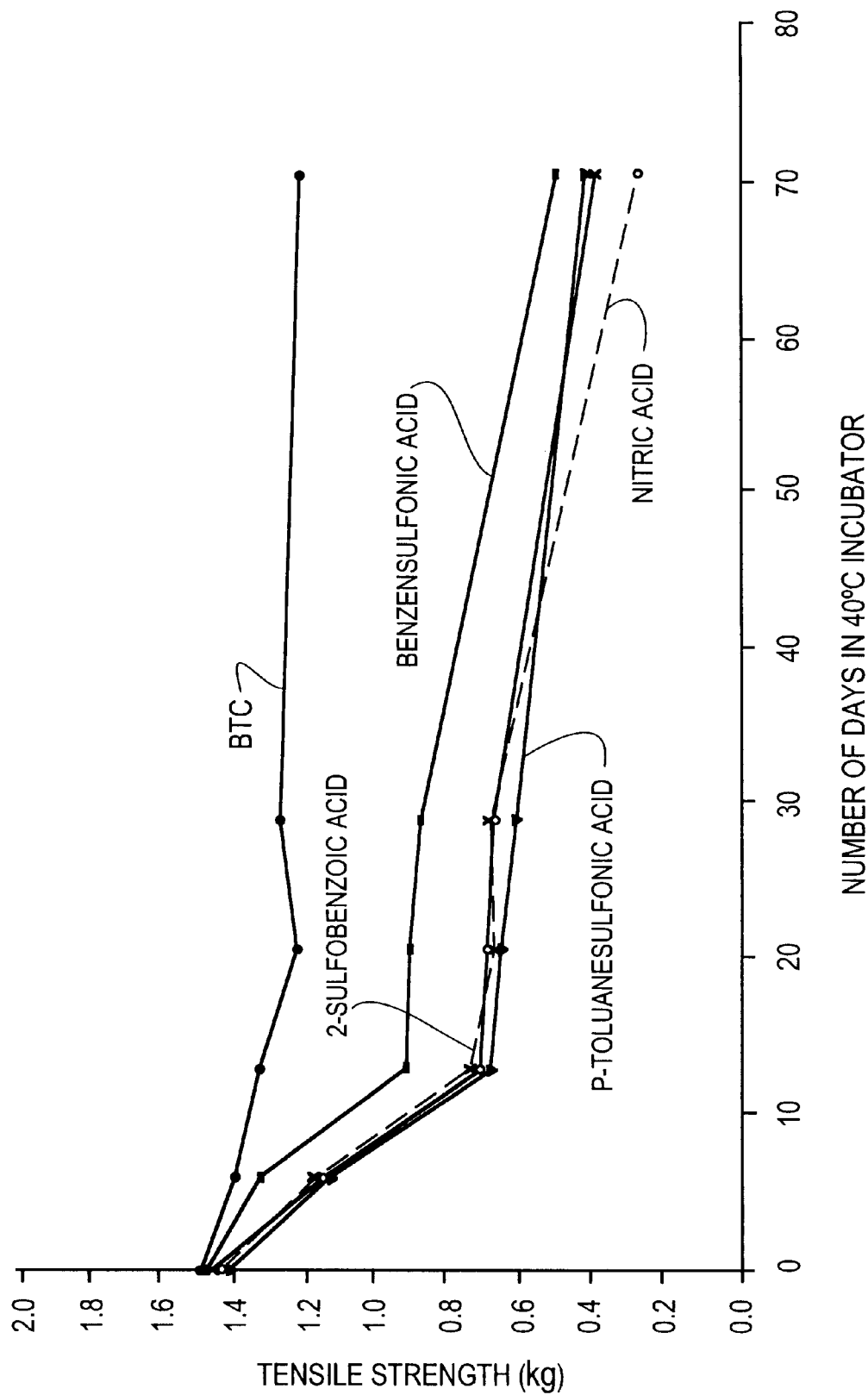
FIG. 1 is a graph of the tensile strengths of hydride detection tapes made using nitric acid, benzenesulfonic acid, p-toluenesulfonic acid, 2-sulfobenzoic acid, and 1,2,4-benzenetricarboxylic acid, measured over time.

In order to evaluate the effectiveness of different formulations for use in hydride detection tapes, a baseline process solution, against which the different formulations would be measured, was prepared. The baseline process solution, or "100N" formulation, was composed of 100 ml of methanol, 1.0 g of silver nitrate, 11 ml of glycerine, and 0.2 ml of concentrated nitric acid. To test the effectiveness of using organic acids in place of nitric acid, a number of different test solutions were prepared. Each test solution was a modification of the "100N" formula, such that the nitric acid was replaced with a different organic acid. The organic acid was added in an amount such that the proton concentration in the resultant processing solution was equal to that of the "100N" solution, assuming complete dissociation of the organic acid.

Test tapes were prepared using cellulose-based porous tapes incorporating an adsorbent such as silica gel and impregnating them with the test solutions and with the "100N" solution. Each test tape was tested for light resistance and for arsine sensitivity. To test for light resistance, the test tapes were exposed to sunlight, and a test tape was deemed to have passed this test if it would not discolor (turn to light pink or gray) in about three to five hours. To test for arsine sensitivity, the test tapes were exposed to arsine gas at a concentration of 50 ppb, which is the threshold limit value (TLV) recommended by ACGIH for arsine, and a test tape was deemed to have passed this test if it formed a stain that was at least as intense as that produced using the "100N" formulation, i.e., that the test tape was at least as sensitive to arsine gas as the "100N" tape.

It was found that only four organic acids from among those tested passed both tests. These four organic acids were: benzenesulfonic acid, p-toluenesulfonic acid, 2-sulfobenzoic acid, and 1,2,4-benzenetricarboxylic acid. Accordingly, each of these organic acids could be used in place of nitric acid in the "100 N" formulation, or may be used in various mixtures that may also include nitric acid, to provide a hydride detection tape having at least some utility.

Test tapes with these four organic acids were then subjected to further tests. The sensitivity of these organic acids, relative to the "100N" formulation, for other hydride gases was tested by exposing the test tapes to silane gas at a concentration of 5 ppm and to germane gas at a concentration of 200 ppb. It was found that the test tapes for benzenesulfonic acid, p-toluenesulfonic acid, and 2-sulfobenzoic acid each had a lower sensitivity to silane gas than the "100N" formulation, but the test tape for 1,2,4-benzenetricarboxylic acid had a higher sensitivity. It was also found that the test tapes for p-toluenesulfonic acid, and 2-sulfobenzoic acid each had a lower sensitivity to germane gas than the "100N" formulation, but the test tape for 1,2,4-benzenetricarboxylic and for benzenesulfonic acid each had a higher sensitivity.

The tensile strengths of each of these test tapes was tested by placing each test tape in an incubator at 40 degrees C. and measuring the tensile strength of each tape over time. The results with respect to 1,2,4-benzenetricarboxylic acid and p-toluenesulfonic acid, as well as the "100N" formulation, are summarized in FIG. 1. As is evident from FIG. 1, the tapes incorporating p-toluenesulfonic acid and 2-sulfobenzoic acid exhibited a degradation in tensile strength over time that was similar to that of the "100N" formulation. However, the benzenesulfonic acid test tape maintained its tensile strength somewhat better than the "100N" formulation, and the 1,2,4-benzenetricarboxylic acid test tape maintained its tensile very much better. Accordingly, from among the four organic acids, 1,2,4-benzenetricarboxylic acid ("BTC") and benzenesulfonic acid are preferred because they result in an improved sensitivity to germane and an improved tensile strength, and 1,2,4-benzenetricarboxylic acid is most preferred because it results in the highest sensitivity to silane and the most improved tensile strength. Two isomers 1,3,5-benzenetricarboxylic acid and 1,2,3-benzenetricarboxylic acid appear to give similar improvement in tensile strength but sensitivity was not as good with the 1,3,5 isomer and difficult to reproduce from batch to batch with the 1,2,3 isomer.

A disadvantage that was found with respect to using 1,2,4-benzenetricarboxylic acid (herein after sometimes abbreviated as BTC) in place of nitric acid is that the resulting tape exhibits a slight degree of light sensitivity. In particular, the edges of the tape are observed to turn light gray after exposure to light. It was found that the tape's light resistance can be improved by using a mixture of BTC and nitric acid. To evaluate the effect of such mixtures on tape tensile strength, another set of test tapes was prepared using only nitric acid, only 1,2,4-benzenetricarboxylic acid, and mixtures of the two acids. The resulting test tapes were placed in an incubator at 40 degrees C., and their tensile strengths were measured over time. The results are summarized in FIG. 2 for each of these formulations. The "100N" formulation was as previously described. The "40N" formulation includes the same amount of methanol, silver nitrate, and glycerine as in the "100N" formulation but to this only 40% by volume of nitric acid was used as compared to the "100N" formulation, i.e., only 0.08 ml of nitric acid was used. The "BTC" formulation includes the same amount of methanol, silver nitrate, and glycerine as in the "100N" formulation but to this was added an amount of BTC sufficient to result in a proton concentration equal to that of the "100N" solution.

The "BTC/10N" formulation was made with the same molar concentration of 1,2,4-benzenetricarboxylic acid as in the "BTC" formulation, but to this was added concentrated nitric acid in an amount such that the molar concentration of nitric acid was approximately 10% that of the "100N" formulation. Similarly, the "BTC/20N" and "BTC/40N" formulations had molar concentrations of nitric acid that were approximately 20% and 40%, respectively, that of the "100N" formulation.

Figure 2:
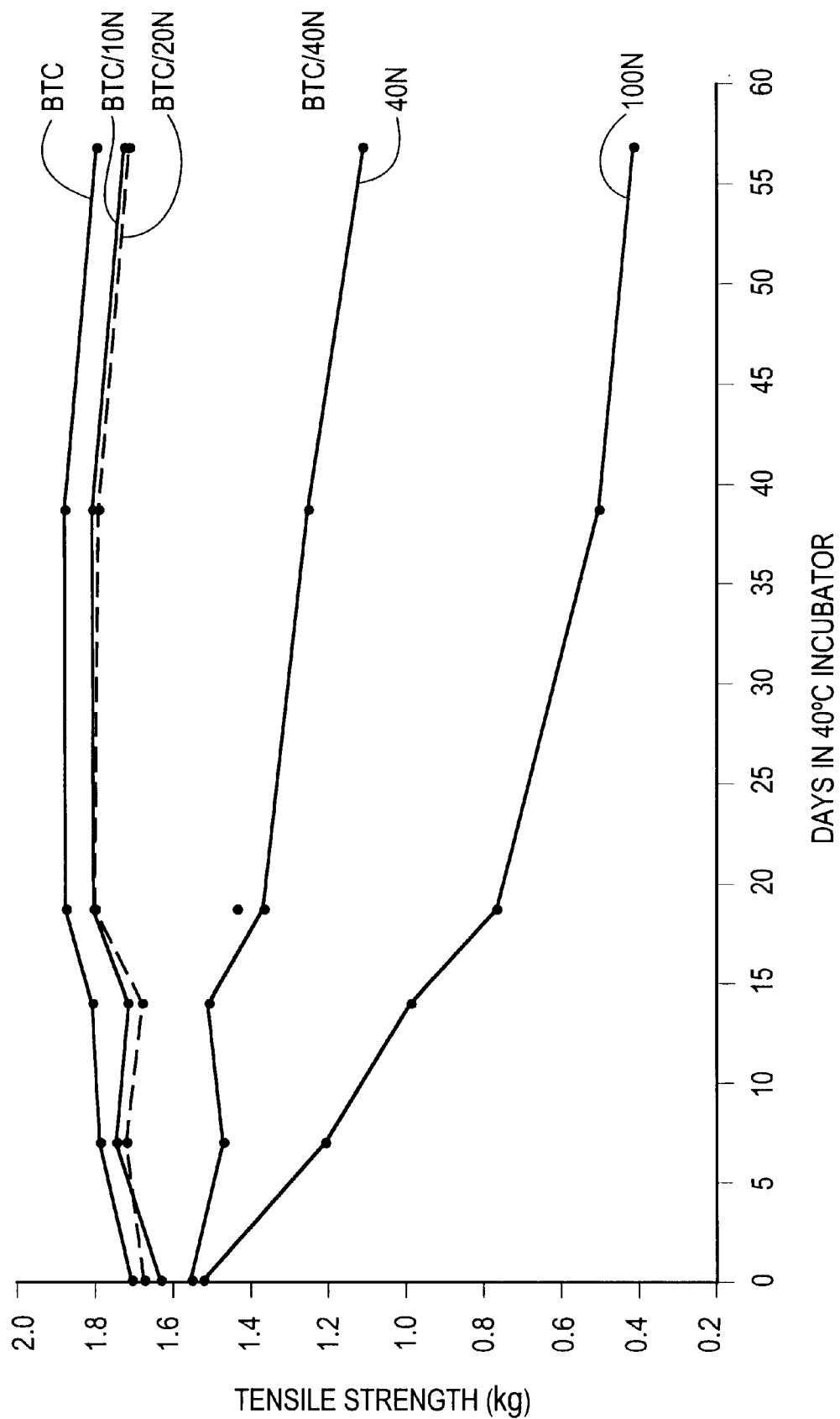
FIG. 2 is a graph of the tensile strengths of hydride detection tapes made using nitric acid, 1,2,4-benzenetricarboxylic acid, and mixtures thereof, measured over time.

As is evident from FIG. 2, the tensile strengths of the "BTC/10N" and "BTC/20N" test tapes remained nearly as high as the tensile strength of the "BTC" test tape. Accordingly, it is preferable to have the molar concentration of nitric acid no greater than about 60% of the molar concentration of 1,2,4-benzenetricarboxylic acid, which corresponds to the ratio found in the "BTC/20N" formulation, so that the resulting tape will maintain a high tensile strength.

To evaluate sensitivities to the hydride gases, six test formulations, designated XP-1 through XP-6, were made using mixtures of 1,2,4-benzenetricarboxylic acid and nitric acid. The compositions of these six test formulations are summarized in Table 1, wherein each batch also included 25 liters of methanol, 250 grams of silver nitrate, and 2.75 liters of glycerine.

TABLE 1

| Formula label | Acid amount in each batch | | AsH3 | B2H6 | GeH4 | SiH4 | PH3 |
|---|---|---|---|---|---|---|---|
| | BTC (g) | HNO3 (ml) | Relative response | | | | |
| 100N | 0 | 50 | 100% | 100% | 100% | 100% | 100% |
| XP-1 | 18 | 10 | 200% | 193% | 256% | 140% | 138% |
| XP-2 | 18 | 5 | 186% | 203% | 219% | 174% | 133% |
| XP-3 | 22.5 | 5 | 181% | 209% | 201% | 186% | 129% |
| XP-4 | 22.5 | 10 | 203% | 191% | 193% | 160% | 137% |
| XP-5 | 36 | 5 | 203% | 203% | 242% | 206% | 137% |
| XP-6 | 60 | 5 | 178% | 194% | 152% | 112% | 133% |

Figure 3:
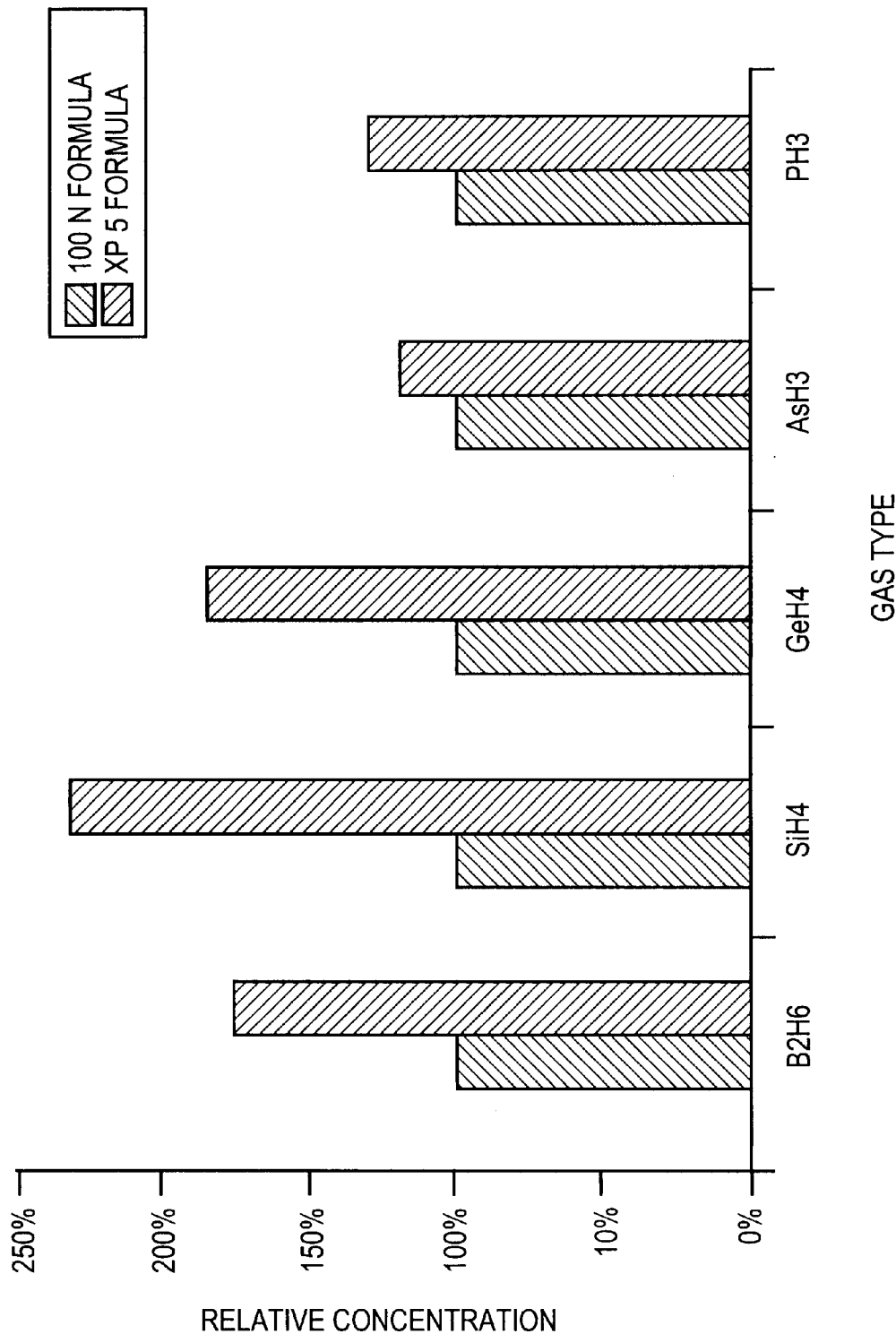
FIG. 3 is a bar graph comparing the hydride sensitivities of the preferred hydride detection tape and a hydride detection tape containing nitric acid.

Each test tape was exposed to each of the five hydride gases at a concentration equal to one-half to one TLV for that gas. The table reports the intensity of the stain resulting from such exposure relative to the 100N formulation. As the table makes evident, each of the formulations XP-1 through XP-6 results in a greater sensitivity to all of the hydride gases, as compared to nitric acid alone. Accordingly, a solution containing from about, 0.072 to 0.24 grams of 1,2,4-benzenetricarboxylic acid for every gram of silver nitrate, which corresponds to the ratios found in the XP formulations, is preferable. However, the "XP-5" formulation is deemed to be the most preferred because it results in the most well balanced sensitivity with respect to the five hydride gases. Accordingly, the most preferred formulation has about 0.144 grams of 1,2,4-benzenetricarboxylic acid for every gram of silver nitrate and has a molar concentration of nitric acid of about 50% of the molar concentration of 1,2,4-benzenetricarboxylic acid, which corresponds to the "XP-5" formulation. The increase in sensitivity that the "XP-5" formulation exhibits over the "100N" formulation is shown for each hydride gas in the bar graph of FIG. 3.

Figure 4:
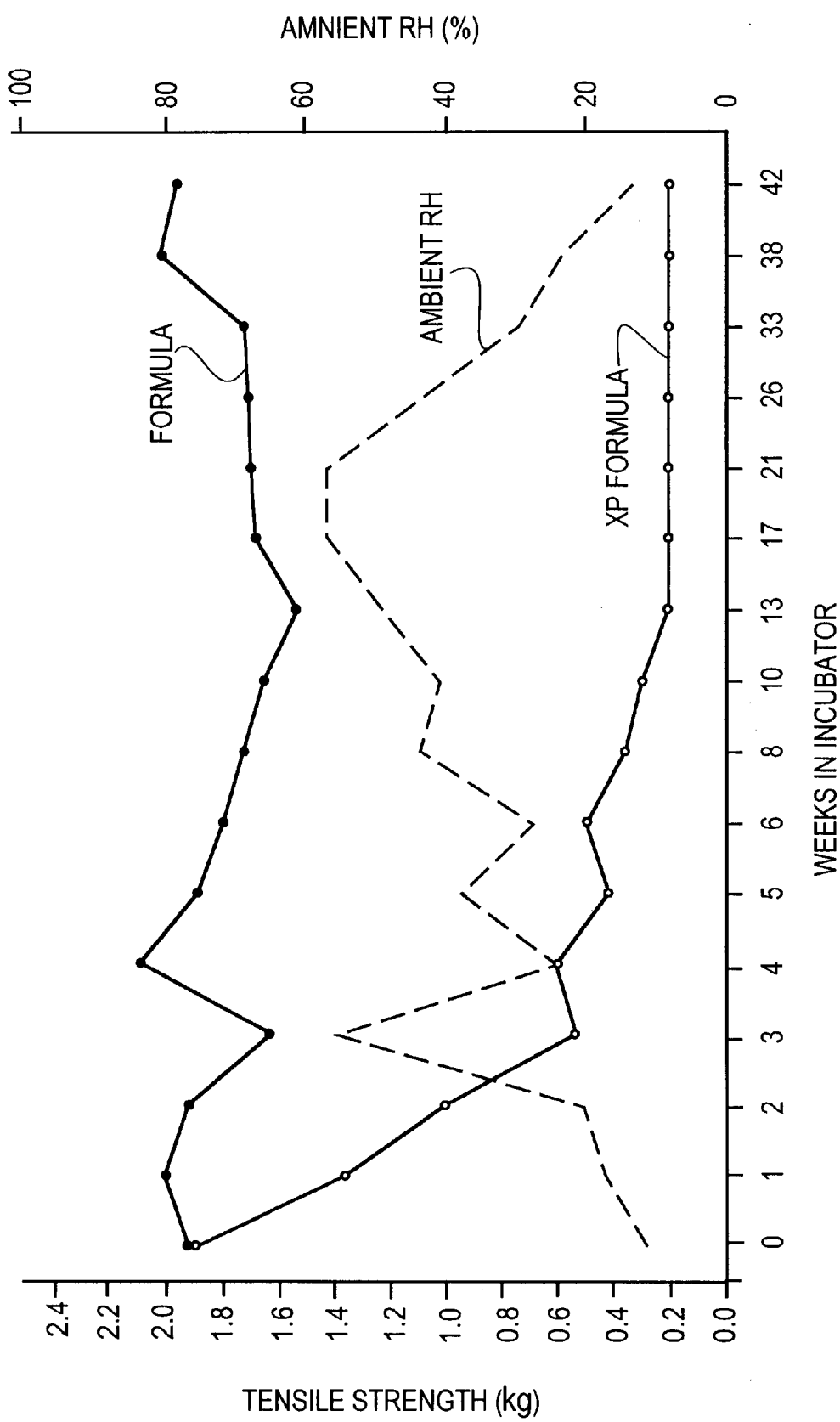
FIG. 4 is a graph comparing the tensile strengths of the preferred hydride detection tape and a hydride detection tape containing nitric acid, measured over time.

Finally, the tensile strengths of tapes made from the "XP-5" and "100N" formulations were tested by placing them in an incubator at 40 degrees C. and measuring their tensile strengths over time. The results are shown in FIG. 4. The relative humidity at each time is also indicated in FIG. 4 because high humidity reduces tape tensile strength. As is evident from FIG. 4, after 17 weeks the tensile strength of the "100N" tape was reduced to nearly zero while the tensile strength of the "XP-5" remained about the same as when it started. Accordingly, the "XP-5" formulation was found to greatly reduce the problem of tensile strength degradation over time, to result in a much higher sensitivity to hydride gases, and to maintain good light resistance. Other silver salts can be used in place of silver nitrate provided they are able to be solubilized. In particular, silver tetra fluoroborate, silver p-toluenesulfonate, silver trifluoromethanesulfonate, silver trifluoroacetate, silver perchlorate have been tested and found to work although not as well as silver nitrate which is, therefore, preferred.

The above described embodiments are merely illustrative of the features and advantages of the present invention. Other arrangements and advantages may be devised by those skilled in the art without departing from the spirit and scope of the present invention. Accordingly, the invention should not be deemed to be limited to the above detailed description but only by the claims that follow.

What is claimed is:

1. A substrate for detecting hydride gases comprising:

a porous substrate incorporating an adsorbent material;

a solution impregnating said adsorbent material, said solution comprising a glycol, a soluble silver salt, and an organic acid selected from the group consisting of benzenetricarboxylic acid, 2-sulfobenzoic acid, and benzenesulfonic acid, whereby said substrate is capable of reaction with a hydride gas for the development of color as a measure of the hydride concentration.

2. A substrate according to claim 1, wherein said substrate is a porous tape.

3. A substrate according to claim 2, wherein said porous tape contains cellulose.

4. A substrate according to claim 1, wherein said solution further comprises an alcohol.

5. A substrate according to claim 4, wherein said alcohol is selected from the group consisting of methanol, ethanol, and isopropanol.

6. A substrate according to claim 5, wherein said alcohol is methanol.

7. A substrate according to claim 1, wherein said adsorbent material is selected from the group consisting of silicic acid, magnesium silicate, magnesium oxide, and aluminum oxide.

8. A substrate according to claim 1, wherein said organic acid is selected from the group consisting of 1,2,4-benzenetricarboxylic acid and benzenesulfonic acid.

9. A substrate according to claim 8, wherein said organic acid is 1,2,4-benzenetricarboxylic acid.

10. A substrate according to claim 9, wherein said solution further comprises nitric acid.

11. A substrate according to claim 10, wherein said solution comprises nitric acid present in a molar concentration that ranges from zero to about one hundred percent of the molar concentration of 1,2,4-benzenetricarboxylic acid.

12. A substrate according to claim 11, wherein said solution further comprises nitric acid present in a molar concentration that is about fifty percent of the molar concentration of 1,2,4-benzenetricarboxylic acid.

13. A substrate according to claim 10, 11, or 12, wherein said solution comprises from about 0.072 to 0.24 grams of 1,2,4-benzenetricarboxylic acid for every gram of silver salt.

14. A substrate according to claim 10, 11, or 12, wherein said solution comprises about 0.144 grams of 1,2,4-benzenetricarboxylic acid for every gram of silver salt.

15. A substate according to claim 1 wherein said soluble silver salt is silver nitrate.

* * * * *